United States Patent [19]

Bobo, Jr. et al.

[11] Patent Number: 5,586,555
[45] Date of Patent: Dec. 24, 1996

[54] BLOOD PRESSURE MONITORING PAD ASSEMBLY AND METHOD

[75] Inventors: Donald E. Bobo, Jr., Orange; Thomas H. Doupe, Huntington Beach, both of Calif.

[73] Assignee: Innerspace, Inc., Santa Ana, Calif.

[21] Appl. No.: 316,555

[22] Filed: Sep. 30, 1994

[51] Int. Cl.⁶ .................................................. A61B 5/00
[52] U.S. Cl. .................................... 128/672; 128/687
[58] Field of Search ............................... 606/201–203; 128/672, 677, 680–687, 689–694

[56] References Cited

U.S. PATENT DOCUMENTS

| | | |
|---|---|---|
| 4,901,733 | 2/1990 | Kaida et al. .................... 128/687 |
| 5,022,402 | 6/1991 | Schieberl et al. . |
| 5,195,522 | 3/1993 | Pytel et al. ........................... 128/690 |
| 5,230,342 | 7/1993 | Bobo, Jr. et al. . |
| 5,335,551 | 8/1994 | Ohnishi et al. ..................... 128/672 |
| 5,398,692 | 3/1995 | Hickey ................................ 128/687 |

Primary Examiner—Angela D. Sykes
Assistant Examiner—Robert L. Nasser, Jr.
Attorney, Agent, or Firm—Stephen C. Shear

[57] ABSTRACT

An improved blood pressure monitoring pad assembly and its method of use are disclosed herein. In accordance with a first feature of the pad assembly a release mechanism is used to prevent the pad assembly from detaching from the skin as the bladder is pressurized. In accordance with a second feature, the pad assembly includes a flexible cover movably connected with a flexible base assembly. In accordance with a third feature, the pad assembly incorporates a biflex member.

36 Claims, 6 Drawing Sheets

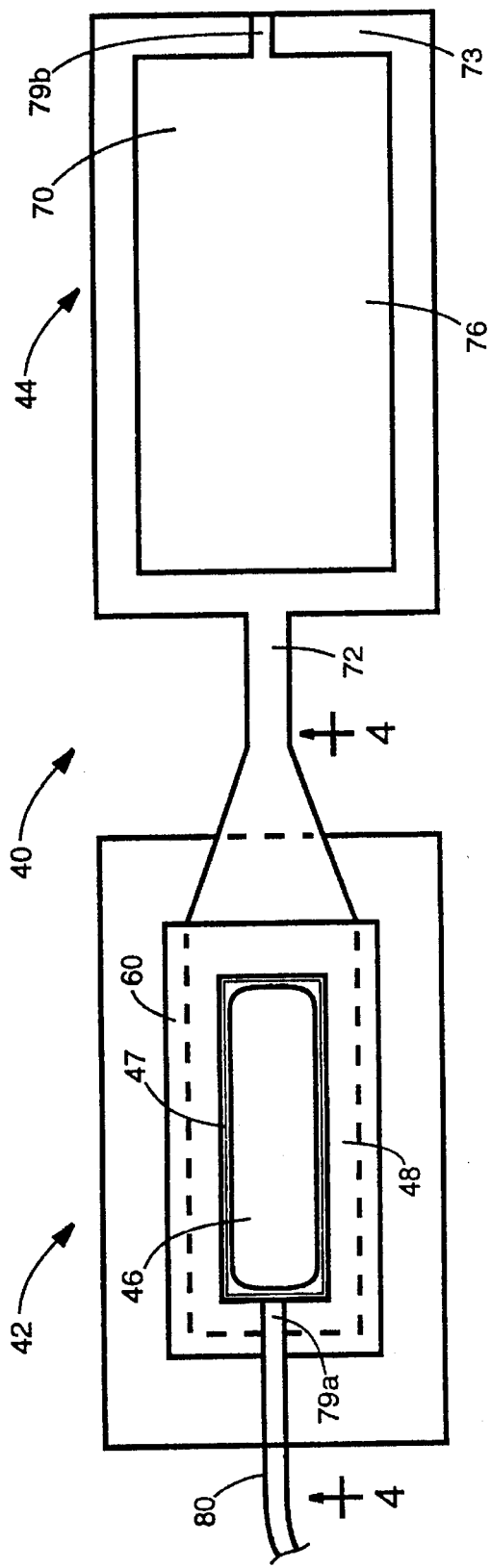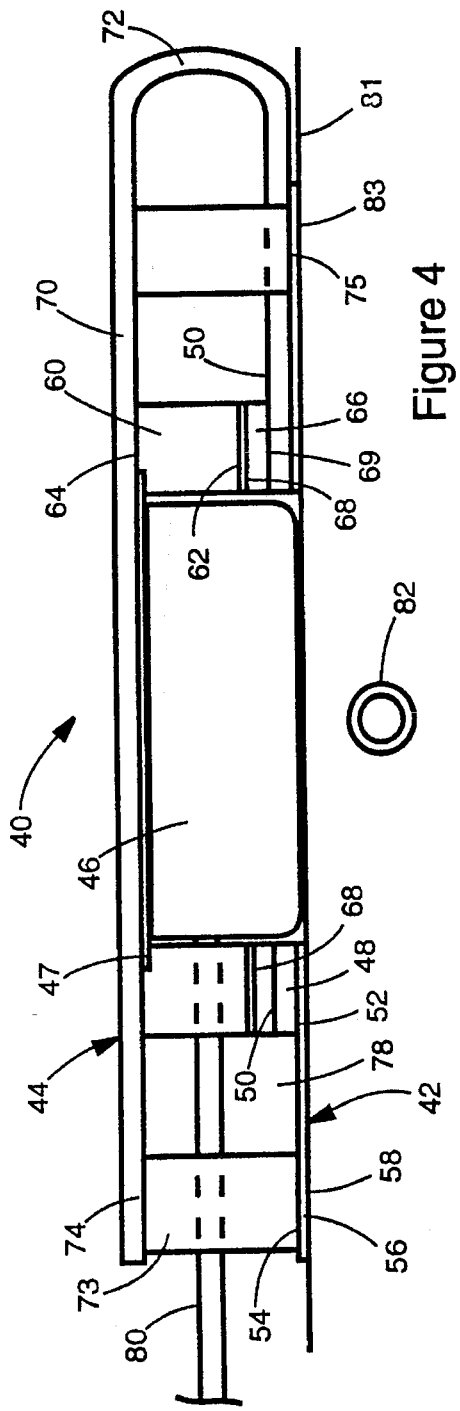

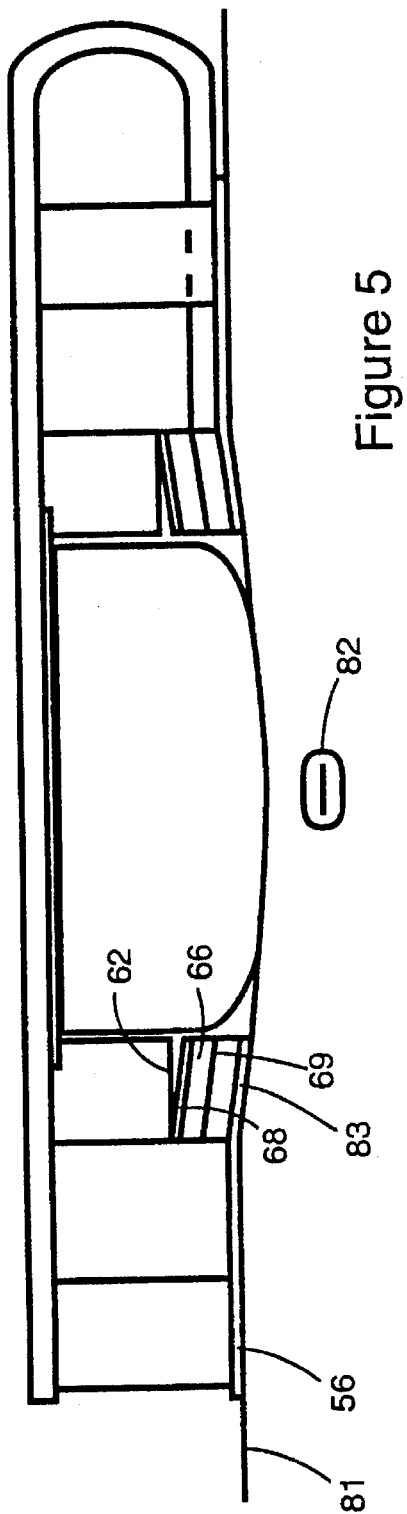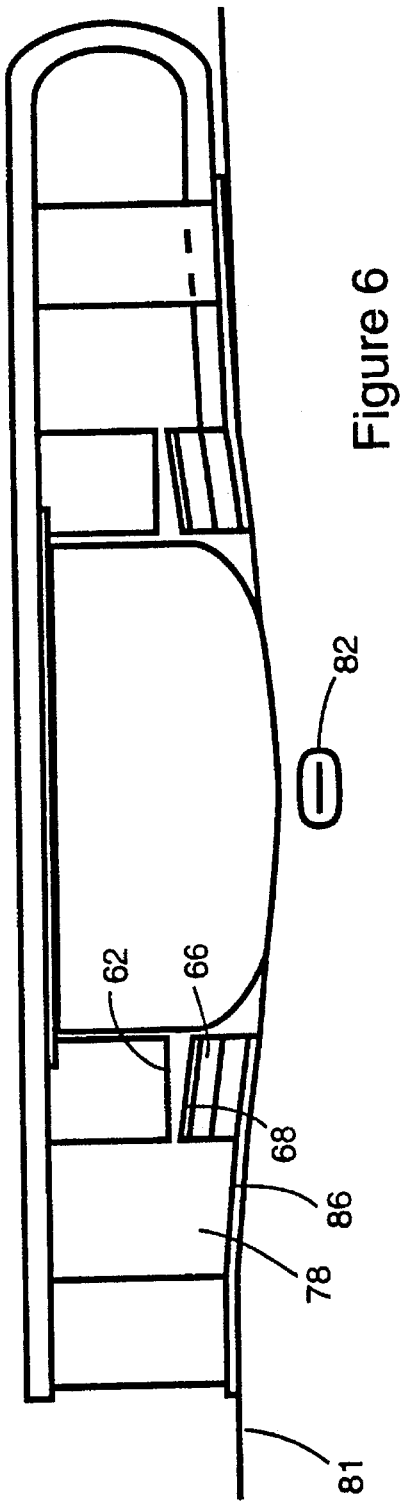

BLOOD PRESSURE MONITORING PAD ASSEMBLY AND METHOD

BACKGROUND OF THE INVENTION

The present invention relates generally to blood pressure monitoring, and more particularly to a blood pressure monitoring pad assembly which is especially designed to take the blood pressure of a patient at a supraorbital artery and to methods for using the pad assembly.

The blood pressure monitoring pad assembly of the present invention is designed for use with oscillometric blood pressure monitoring techniques which are well known in the art. In U.S. Pat. No. 5,230,342, which is incorporated herein by reference, techniques are disclosed for utilizing the supraorbital artery of a patient to measure the blood pressure of the patient along with a blood pressure monitoring pad assembly for use in implementation of these techniques. The blood pressure monitoring pad assembly of the present invention represents an improved version of a pad assembly for use with a supraorbital artery of a person. Techniques for using the improved monitoring assembly of the present invention are also disclosed herein.

FIGS. 1 and 2, taken directly from the '342 patent, are diagrammatic illustrations of a prior art blood pressure monitoring pad system which is generally indicated by the reference numeral 10. The system includes a blood pressure monitoring pad assembly 16 including a pressufizable pressure transducing bladder 18 mounted to a larger and more rigid bladder backing 19. A pad 20 has an adhesive backing 22 against which bladder 18 and backing 19 are fixedly mounted. The pad 20 has an outermost configuration which, when applied to the patient in accordance with a method of the patent, properly positions bladder 18 in order to locate and access a supraorbital artery. The assembly is adhesively attached to the forehead of the patient by adhesive backing 22 to be held in the proper position for the duration of the monitoring procedure.

While the blood pressure monitoring pad assembly, as depicted in FIGS. 1 and 2, does permit measurement of the blood pressure at the location of the supraorbital artery and is generally satisfactory for its intended purpose, there are several particular aspects of this assembly that can be improved upon, as will be discussed below.

One such improvement relates to the pressurization of the bladder which causes a force to be directed outwardly from the patient's skin in response to the inward force of the bladder against the skin. This outward force is transferred from the side of the bladder opposite the skin to backing 19 and pad 20. The outward force is applied directly to adhesive backing 22 from pad 20 and thereby to the adhesive bond between the pad assembly and the skin on the patient's forehead. The pad assembly itself is internally constructed in a manner such that the adhesive bond between backing 19 and pad 20 is typically quite strong requiring a force significantly greater than that caused by pressurization of the bladder to break it. The weakest and least reliable bond forming part of the pad assembly is generally the bond between the pad assembly itself and the biological skin on the forehead of the patient. The force which is applied to this adhesive bond by pressurization of the bladder is a peel force. Traditionally adhesives are more resistant to shear forces than peel forces. Once the peel has begun, less force is typically required to propagate the peel. This bond is therefore predisposed to failure in a generally gradual manner in which the bond has a tendency to begin to separate immediately adjacent to the bladder. With repeated pressurization cycles, continuous pressurization or overpressurization, the bond between the skin and the pad assembly is likely to continue to separate.

Separation of the pad assembly from the skin forms an additional space surrounding the bladder in which the bladder is able to freely inflate and deflate during pressurization cycles and, in fact, the bladder has a tendency to fill this additional space during pressurization before applying a significant downward force to the skin whereby to engage the target artery. If the additional space is permitted to reach a large enough volume relative to the bladder, the bladder will be rendered unable to properly engage the skin and the target artery below. Upon continued separation of the adhesive bond between the pad assembly and the skin, the pad assembly may become completely detached from the skin.

An obvious solution to this problem is to use a very strong adhesive to bond the pad assembly to the skin. The adhesive presently in use is one of the strongest available and it is a concern that a stronger adhesive could possibly cause discomfort or, in some cases, even trauma.

A second possible area of improvement of the pad assembly shown in FIGS. 1 and 2 resides in the fact that it is relatively rigid in order to properly support the bladder against the forehead at the location of the supraorbital artery. Since the forehead of most individuals is relatively planar vertically, the pad assembly is capable of conforming to the forehead from top to bottom at the location of the supraorbital artery. Conforming to the curvature of the forehead horizontally, that is, from side to side is a much more difficult matter using the pad assembly as shown, since the horizontal curvature is much less planar. It has been found that the horizontal curvature of the forehead of typical individuals about a vertical axis can vary by as much as a factor of two to one. Due to the fact that the pad assembly is relatively rigid, upon conforming it to an individual's forehead, stress is created within the pad assembly. The greater the curvature of the individual's forehead the greater will be the stress induced within the pad assembly upon application to the subject's forehead. This stress may, in and of itself, lead to a failure of the adhesive bond between the monitoring pad assembly and the skin of the forehead and, in combination with the stress upon the adhesive skin bond due to pressurization of the bladder, can lead to premature failure of the bond with the skin.

It is desirable, in view of the prior art discussed above, to provide a blood pressure monitoring pad assembly for use with a supraorbital artery of a person which will remain operationally attached to the person's forehead and functional for a desirable period of time while still providing for the comfort of the person and, further, to provide a pad assembly which is sufficiently rigid when in use to properly support the bladder during pressurization and yet is sufficiently flexible during the application of the pad assembly to the person's forehead to conform to the shape of the person's forehead at the location of the supraorbital artery, even in cases of relatively sharp horizontal curvature of the forehead about the vertical axis.

SUMMARY OF THE INVENTION

As will be described in more detail hereinafter, a blood pressure monitoring pad assembly and method of it using are disclosed herein. This assembly, like the assembly in FIGS. 1 and 2, includes provisions for monitoring the blood pressure of a person when adhesively attached to the skin of the person at the location of a target artery. However, in accordance with a first feature of the present invention, a pad assembly including a pressure transducing bladder is supported to the skin of the person by support means including adhesive tape so that the adhesive tape is directly attached to the skin adjacent the bladder with the bladder adjacent the target artery. The support means includes an arrangement configured to move in response to the pressurization of the bladder in a way which prevents the adhesive tape from detaching from the skin as the bladder is pressurized.

In accordance with a second feature of the of the present invention, a pressure transducing bladder is supported in place against the target artery by a base assembly including adhesive tape such that the bladder is in direct contact with the skin adjacent the target artery and the adhesive tape is directly attached to a portion of the skin adjacent the bladder. A cover assembly is connected to the base assembly for movement between a separated or open position apart from the base assembly and a closed position in which the cover assembly is placed directly against the base assembly and fixedly attached thereto to provide a backing for the bladder.

In accordance with a third feature of the present invention, a pressure transducing bladder is supported in place against the target artery by support means including adhesive tape such that the bladder is in direct contact with the skin adjacent the target artery and the adhesive tape is attached directly to a portion of the skin adjacent the bladder. The support means includes a biflex member which displays a greater flexibility in one predetermined direction than in another predetermined transverse direction.

A first method for using a blood pressure monitoring pad assembly of the type including the first feature of the present invention includes providing a flexible base assembly including the bladder attached to the base assembly and further providing a cover assembly connected to the base assembly for movement between positions spaced apart from and directly adjacent the base assembly. With the cover assembly in its spaced apart position, the base assembly is adhered to the person's skin so that it conforms to the contour thereof and so that the bladder directly contacts the skin adjacent to the target artery. Thereafter the cover assembly is moved to its adjacent position against said base assembly so as to conform to the contour of base assembly and bond the two together. This cover assembly could also be separate from (not connected) to the base assembly, but still closed against the base assembly and the bladder could be connected to the cover assembly rather than the base assembly.

A second method for using a blood pressure monitoring pad assembly of the type including the second feature of the present invention includes adhesively placing a blood pressure monitoring pad assembly including the bladder and support means for supporting the bladder on the skin of the person to form an adhesive bond between the skin and the monitoring pad assembly such that the bladder is brought into direct contact with the skin adjacent the target artery, pressurizing the bladder to bring the bladder into communication with the target artery and providing an arrangement within the support means configured to move within a release zone in a way which prevents the adhesive tape from detaching from the skin during pressurization of the bladder.

BRIEF DESCRIPTION OF THE DRAWINGS

The present invention may be understood by reference to the following detailed description taken in conjunction with the drawings in which:

FIG. 3 is a diagrammatic plan view of a first embodiment of a blood pressure monitoring pad assembly which is shown including a base assembly and a cover assembly designed in accordance with the present invention.

FIG. 4 is a cross-sectional view in elevation of the base assembly forming part of the pad assembly of FIG. 3 shown attached to a person's skin over a target artery with the cover assembly of FIG. 3 directly attached to the base assembly.

FIG. 5 is a cross-sectional view in elevation of the pad assembly of FIG. 4 attached to the skin of a person adjacent the supraorbital artery to illustrate a feature of its operation.

FIG. 6 is a cross-sectional view in elevation of the pad assembly of FIG. 4 attached to the skin of a person adjacent the supraorbital artery to illustrate another feature of its operation.

DETAILED DESCRIPTION OF THE INVENTION

Figure 1:
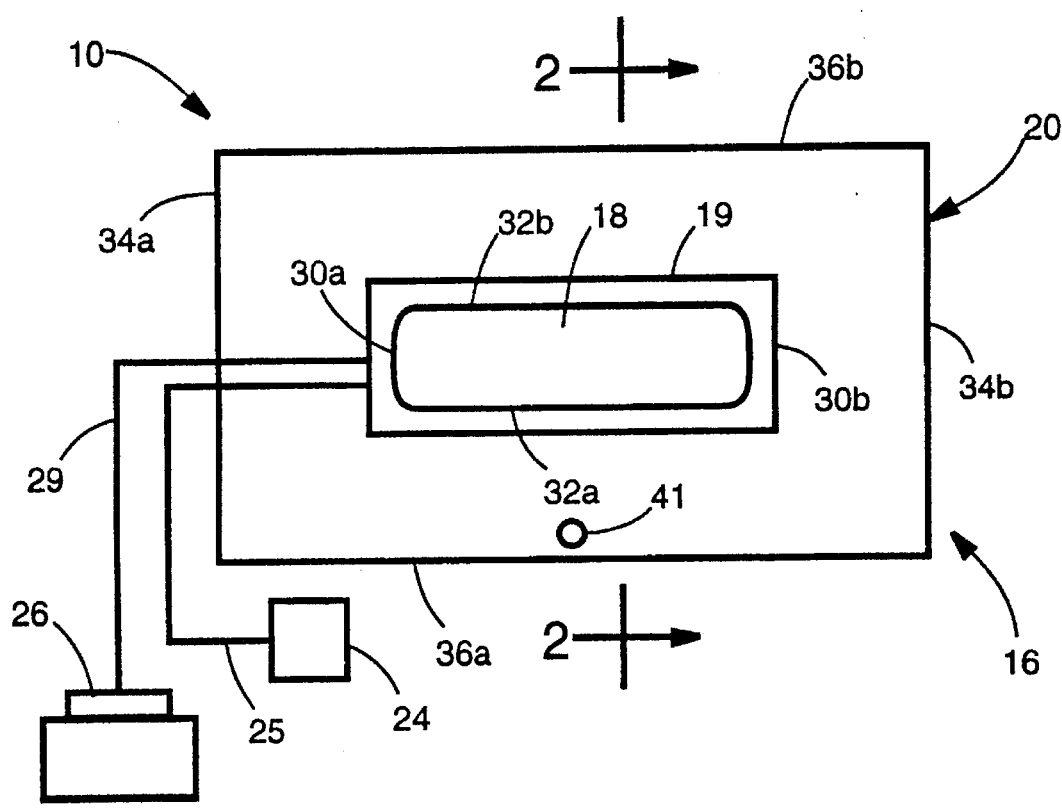
FIG. 1 is a diagrammatic illustration of a prior art blood pressure monitoring pad assembly taken from U.S. Pat. No. 5,230,342.
Figure 2:
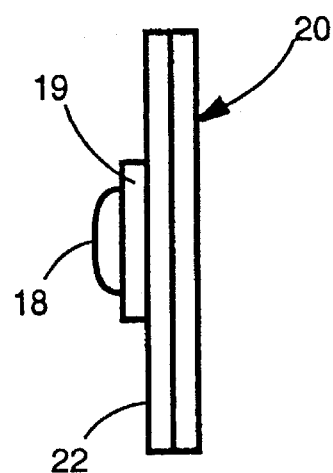
FIG. 2 is a sectional view of the pad assembly of FIG. 1 taken generally along line 2—2 in FIG. 1 which is also taken from U.S. Pat. No. 5,230,342.

Having described FIGS. 1 and 2 previously, attention is immediately directed to FIGS. 3 and 4 which illustrate a first embodiment of a blood pressure monitoring pad assembly manufactured in accordance with the present invention and generally designated by reference numeral 40. The pad assembly includes a base assembly 42 and a cover assembly 44, shown in FIG. 3 separated from one another and in FIG. 4 in a position such that cover assembly 44 is directly against base assembly 42.

Still referring to FIGS. 3 and 4, the base assembly includes a pressure transducing bladder 46 having a surrounding upper flange 47. A base 48 surrounds the bladder and includes an upper surface and a lower surface 50 and 52, respectively. Base 48 is formed from a plastic sheet material which may be rigid PVC. Many other materials may be found suitable for this application provided that they have characteristics of flexibility and strength comparable with rigid PVC. Lower surface 52 of the base is bonded to an upper adhesive surface 54 of an adhesive tape 56 which also surrounds the bladder. Adhesive tape 56 is double sided and therefore includes a lower adhesive surface 58. Avery 445 skin tape has been found to be suitable for use as the adhesive tape, although any strongly adhering tape suitable for application to skin may be used. The bond between upper surface 54 of the adhesive tape and lower surface 52 of the base comprises a strong bond for several reasons. Firstly, adhesive tape 56 is a strongly adhering tape in comparison to most other adhesive tapes, especially among those designed for use in medical applications for bonding to skin, and, secondly, adhesive bonds between manmade materials such as plastic and tape, as is the case here, are characteristically strong.

An inner frame 60 including a lower surface 62, which may optionally be adhesive, and an upper adhesive surface 64 also surrounds bladder 46. In FIG. 4 it can be seen that upper flange 47 on the bladder is adhesively secured to upper adhesive surface 64 of the inner frame. Any other method of securing the bladder in the pad assembly may be utilized provided that it is compatible with the present invention. The inner frame, like base 48, must display sufficient flexibility and strength to be useful in this application. plastic foam materials have been found to be suitable, although many other materials could possibly be used. Lower surface 62 of the inner frame is adhesively bonded to a portion of upper surface 50 of base 48 by a layer of double sided release tape 66 which is specifically chosen for its adhesive characteristics in bonding to lower surface 62. In particular, a release bond 68 is formed by the release tape with lower surface 62 of the inner frame, in accordance with a feature of the present invention. A lower adhesive surface 69 of the release tape also, in turn, forms a strong bond with upper surface 50 of the base. The characteristics of release bond 68 will be described hereinafter, following the description of further derails of the structure of the invention.

Continuing and referring now specifically to FIG. 3, cover assembly 44 includes a backing 70 which is formed from the same plastic sheet material as base 48 in the base assembly such that backing 70 is flexibly connected to the base by a narrow neck portion 72 of the plastic sheet to flexibly connect cover assembly 44 to base assembly 42 for movement of the cover assembly between an open position separated from the base assembly, as shown in FIG. 3, and another position in which the cover assembly is in direct contact with and bonded to the base assembly, as shown in FIG. 4. Other connecting elements or means may be provided to flexibly connect the cover assembly to the base assembly and, in fact, the cover and base assemblies may be separately provided, in accordance with the present invention.

Cover assembly 44 further includes an outer frame 73 having an upper surface 74, as seen in FIG. 4, which is fixedly attached to backing 70 and a lower surface 75 for adhesive bonding to the base assembly when the cover assembly is placed in the closed position. The outer frame may be comprised of the same material as inner frame 60, such as plastic foam. Outer frame 73, in FIG. 3, is configured to have a central opening 76 such that when the cover assembly is placed in the closed position the outer frame surrounds the inner frame at a predetermined lateral distance therefrom to define a stop gap 78, shown in FIG. 4, between the inner and outer frames which will later be described in detail.

Referring again to FIG. 3, inner frame 60 and outer frame 73 each include a respective notch 79a and 79b for the passage of a tube 80 which is directly connected to the bladder for pressurization of the bladder from an external source. Any other suitable means of routing tube 80 through the pad assembly to the bladder may be utilized.

Initially, prior to application to a person, the pad assembly is received with the cover assembly in a position separated from the base assembly, as shown in FIG. 3. The base assembly apart from the cover assembly is designed so as to be sufficiently flexible in order to conform to a portion of skin 81, shown in FIG. 4, on the forehead of a person at the location of a supraorbital artery 82 during its application thereto. The base assembly is conformingly adhered to the skin 81 on the forehead of the person by bottom adhesive surface 58 of adhesive tape 56, such that bladder 46 directly contacts skin 81 adjacent supraorbital artery 82 to form a strong adhesive bond 83 between the skin and the adhesive tape. Adhesive bond 83 is critical to the proper operation of the pad assembly and care must be taken to insure that this bond is as strong as possible. For example, the skin should be very clean prior to application of the pad assembly. Prior to adhesion the base assembly must be aligned with certain features of the person's forehead, as discussed in the prior art U.S. Pat. No. 5,230,342 to insure that the bladder is properly positioned to access the supraorbital artery. As the base assembly is adhered to the skin its flexibility apart from the cover assembly insures that it will properly conform to the curvature of the forehead to which it is being adhered, without creating undue stress within the pad assembly, which would place stress directly on adhesive bond 83 and could lead to premature failure of the bond.

After base assembly 42 is adhered to the person's forehead, cover assembly 44 is then brought from its separated position away from the base assembly to a closed position directly against the base assembly, as shown in FIG. 4. The cover assembly is sufficiently flexible apart from the base assembly to insure that it adhesively conforms to the contoured shape of the base assembly on the forehead. As the cover assembly is placed against the base assembly, upper adhesive surface 64 of inner frame 60 adhesively bonds to backing 70 in the cover assembly, or, in the case where flange 47 of the bladder completely covers upper adhesive surface 64 of the inner frame (not shown), other means, such as an additional layer of double sided adhesive tape, may be provided on flange 47 to bond the inner frame to the cover assembly as it is placed in the closed position. Lower adhesive surface 75 of outer foam frame 73 also adhesively bonds with upper surface 54 of adhesive tape 56 which is, in turn, adhesively attached directly to skin 81.

The adhesive bonds formed by the frames to the respective opposing components in the base and cover assemblies comprise relatively strong bonds between manmade materials, as discussed above, and are unlikely to fail in response to pressurization of bladder 46. In addition, backing 70 with the cover assembly closed provides a rigid support for bladder 46 as it is pressurized, in order to cause the bladder to move primarily in a downward direction whereby to apply force to the skin and the target artery there below. The blood pressure monitoring pad assembly with the cover assembly in the closed position provides a conformed rigid containment for surrounding the bladder, in accordance with the present invention, which is significantly more rigid than the cover assembly or the base assembly when considered independently. This conformed rigidity is achieved by the method of application of the base assembly to the person apart from the cover assembly and thereafter bonding the cover assembly to the base assembly.

As bladder 46 is pressurized during operational use of the blood pressure monitoring pad assembly, the pad assembly is designed to respond internally to the forces created by the pressurization in a way which is calculated to maintain adhesive bond 83 between adhesive tape 56 and skin 81 in order to maintain attachment of the pad assembly to the skin. In particular, release bond 68 between release tape 66 and lower surface 62 of the inner frame in the base assembly is a weaker adhesive bond, due to the predetermined adhesive bonding characteristics between the release tape and the lower surface of the inner frame, than adhesive bond 83 between skin 81 and lower surface 58 of adhesive tape 56. At a predetermined point during the pressurization of bladder 46, release bond 68 will begin to incrementally separate, as shown in FIG. 5. As this separation occurs, bond 83 between skin 81 and adhesive tape 56 is maintained, in accordance with the present invention. Continued pressurization of the bladder will cause still further separation of the release bond from the release surface.

If pressurization of the bladder does continue, release bond 68 will eventually separate completely from the inner frame, as is shown in FIG. 6. In this event, stop gap 78 comes into play. With the complete separation of the release bond a relatively broad expanse of skin 86, within the area of the stop gap, becomes available for stretching by the bladder to still further relieve the stress on adhesive bond 83 between the adhesive tape and the skin. In addition, outer foam frame 73 is designed so as to be capable of supporting the bladder in place against supraorbital artery 82 independent of the inner frame in the case of complete separation of the release bond as described above. Further, as long as the inner frame remains attached by means of the release bond the force applied to the outer frame due to pressurization of the bladder is minimized so that the outer frame, if it is called upon to completely support the bladder in place, is in excellent condition, having been more or less protected by the inner frame.

Figure 7:
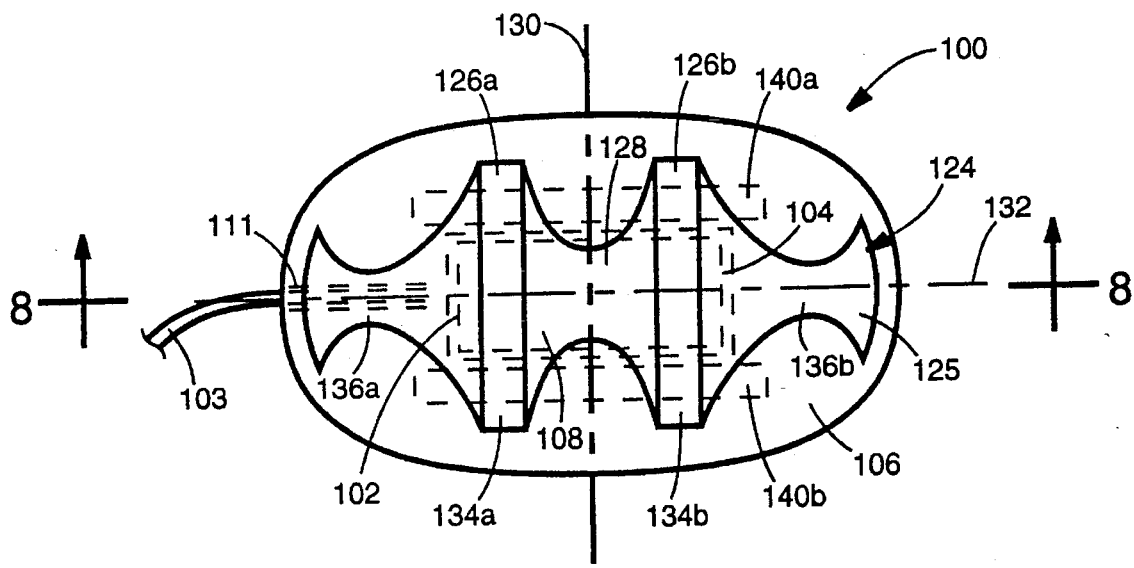
FIG. 7 is a diagrammatic plan view of a second embodiment of a blood pressure monitoring pad assembly designed in accordance with the present invention.
Figure 8:
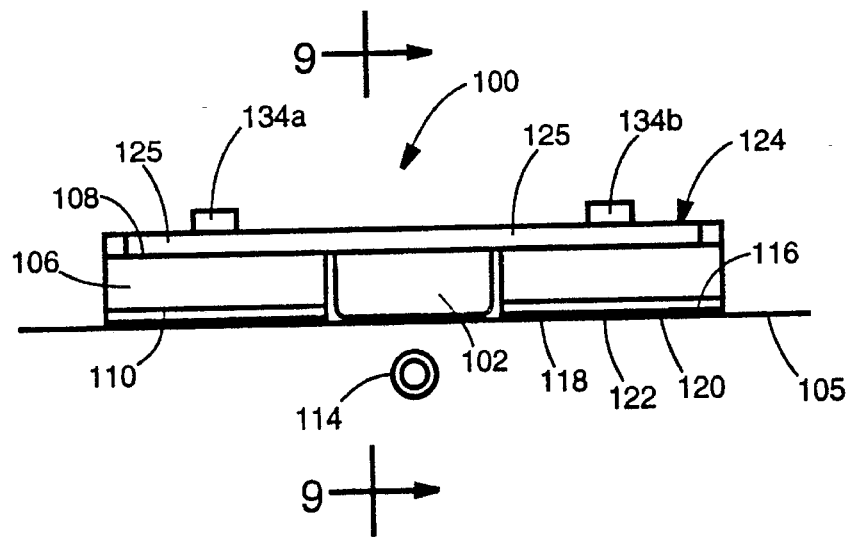
FIG. 8 is a cross-sectional view in elevation of the pad assembly of FIG. 7 shown attached to a person's skin adjacent the supraorbital artery.

A second embodiment of a blood pressure monitoring pad assembly manufactured in accordance with the present invention is shown in FIGS. 7 and 8, and is generally designated by the reference numeral 100. Pad assembly 100 includes a pressurizable pressure transducing bladder 102 including a tube 103 for pressurization of the bladder with either fluid or gaseous media and a surrounding upper flange 104. Upon pressurization, the bladder contacts a portion of a person's skin 105 during the measurement of the person's blood pressure using oscillometric techniques of the prior art.

Referring now to FIG. 8, a frame 106 surrounds bladder 102 and includes an upper adhesive surface 108, a lower adhesive surface 110 and a notch 111 for the passage of tube 103 from its external connections to its connection to the bladder for pressurization of the bladder. Any other means known within the prior art may be used to route the tube to the bladder. A variety of materials may be used for the frame including plastic and plastic type foam material provided that they are adaptable to adhesive bonding, that they are sufficiently flexible and that they are strong enough to resist the forces applied due to pressurization of the bladder.

Upper adhesive surface 108 of the frame is adhesively bonded to flange portion 104 of the bladder to affix the bladder such that the bladder may extend downwardly against a portion of the skin adjacent a target artery 114, which is generally a supraorbital artery. Lower adhesive surface 110 of frame 106 is adhesively bonded to an upper adhesive surface 116 of an adhesive skin tape 118 which also includes a lower adhesive surface 120. Lower adhesive surface 120 is, in turn, bonded directly the skin adjacent bladder 102. The skin tape used must form a bond 122 with the skin which is as strong as possible considering the various factors which come into play when making such a bond, as was previously covered in the discussion regarding the first embodiment of the invention. The adhesive tape used in this embodiment may, in fact, be the same tape as is used to bond the pad assembly to the skin in the first embodiment of the invention, which is Avery 445 skin tape, although other tapes may be found to be suitable.

In accordance with a first feature of the second embodiment of the invention, a biflex member 124, seen in both FIGS. 7 and 8, is adhesively bonded to upper adhesive surface 108 of frame 106. Biflex member 124 includes a backing piece 125 which is typically formed from a plastic sheet material which may be rigid PVC. Backing piece 125 is formed to include a pair of spaced apart, generally parallel leg sections 126a and 126b with an intermediate web section 128 between the respective leg sections to provide more flexibility about a rigid axis 130 substantially parallel to the leg sections and passing through web section 128 than about a flexible axis 132 normal to the leg sections and passing through web section 128, as depicted in FIG. 7. Each of a pair of stiffening strips 134a and 134b is bonded to a respective one of the leg sections 126a and 126b to provide for additional stiffness about rigid axis 132. In the present example, stiffening strips 134a and 134b are adhesively bonded to backing piece 125. The stiffening strips may also be formed from rigid PVC, but many other materials, especially of a plastic composition, may be found to be useful for fabrication of both backing piece 125 and stiffening strips 134a and 134b. Backing piece 125 may also be formed including a pair of outer web sections 136a and 136b each positioned outwardly adjacent a respective leg section and terminating in respective end sections 138a and 138b adjacent each respective outer web section such that the outer web sections provide additional flexibility about the flexible axis while lengthening the biflex member to provide sufficient support to bladder 102.

It is also anticipated here that the biflex member can be fabricated in a molding operation such that the member is molded as a unitary plastic part which is integrally thicker in the area of the stiffening strips to avoid the need for attachment of separate stiffening strips. The outward appearance and geometry of the biflex member are not critical to the invention and it is envisioned that they may be altered significantly while continuing to retain the flexibility characteristics which make the member useful in this application, as described above.

Still referring to FIG. 7, and in accordance with another feature of the present invention, a pair of release tape segments 140a and 140b are shown. Release tape segment 140a is further illustrated in cross-section in FIG. 9. Release tape segment 140b is not shown for purposes of clarity but it is identical to segment 140a, except that it is oppositely positioned with respect to the bladder.

Figure 9:
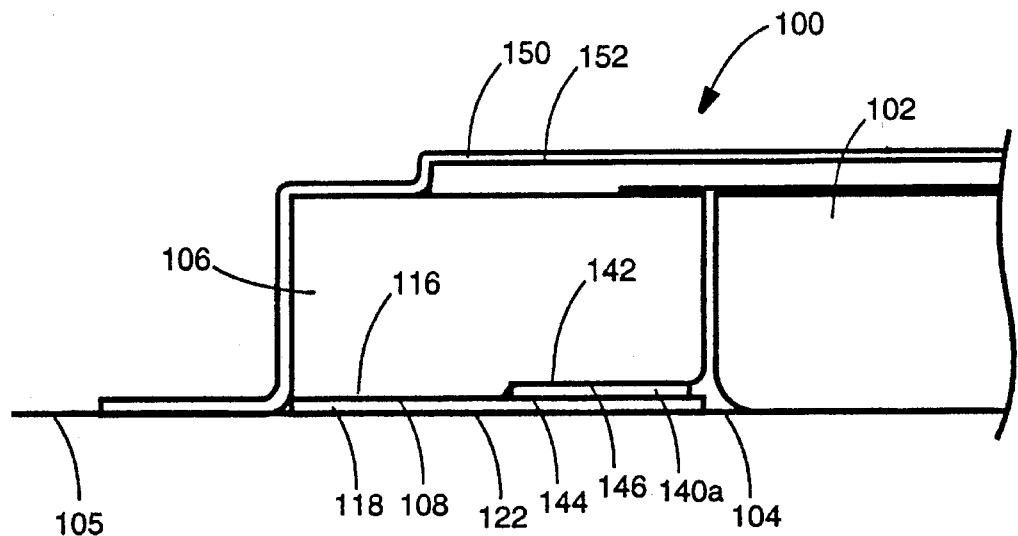
FIG. 9 is a cross-sectional view, in elevation along line 9—9, of a section of the pad assembly of FIG. 8 attached to the skin of a person to illustrate details of the structure without the bladder pressurized.

Referring now to FIG. 9, release tape segment 140a includes upper and lower adhesive surfaces 142 and 144 respectively and is interposed between a predetermined portion of frame 106 and a portion of adhesive tape 118. Lower surface 144 of the release tape segment adhesively bonds with upper surface 116 of adhesive tape 118 to form a bond which is generally stronger than bond 122 between lower surface 120 of the adhesive tape and the skin. A release bond 146, is formed between upper adhesive surface 142 of the release tape segment and the portion of foam frame 106. Release bond 146 is, in contrast, weaker than the bond between tape 118 and the skin and functions in a manner similar to that of the release tape as discussed with regard to the previous embodiment of the invention as the bladder is pressurized.

Disposition of release tape segments 140a and 140b within pad assembly, as illustrated in FIG. 7, is but one possible arrangement proven to be effective. Segments 140a and 140b may be repositioned or additional release tape segments may easily be added and positioned between the frame and the adhesive tape at locations around the bladder to accommodate varying conditions under which the pad assembly may be used, within the scope of the present invention.

Referring again to FIG. 9, pad assembly 100 is further held in place to a portion of the skin surrounding adhesive tape 118 by an overall layer of elastic adhesive tape 150 having an adhesive surface 152. Elastic tape 150 is selected for both its elastic property and its ability to adhesively bond to the exposed portions of the biflex member, the frame and the skin. The elastic tape provides additional attachment support for the pad assembly to the skin and helps to retain the pad assembly in position on the skin during repeated pressurization cycles of the bladder by elastically returning the assembly to its original position following pressurization.

Pad assembly 100 is particularly adapted for use with supraorbital artery 114 of a person. The flexibility characteristics of biflex member 124 within pad assembly 100 provide for proper conformance of the assembly to the skin at the location on the forehead of the supraorbital artery. As discussed previously, the forehead is substantially planar from top to bottom and is characteristically curved from side to side which may vary by as much as a factor of two to one between respective individuals.

Figure 10:
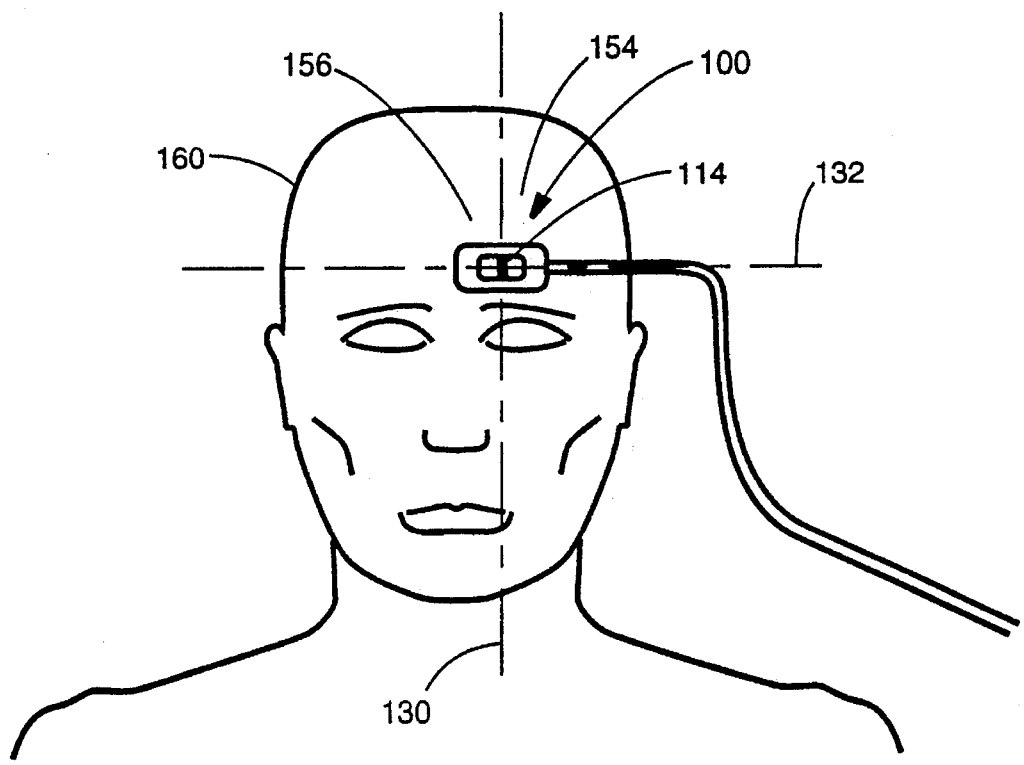
FIG. 10 is an illustration of the proper orientation of the pad assembly of FIG. 7 when it is attached to the forehead of a person.

Initially, prior to application, pad assembly 100 must be properly located by appropriate means, as discussed in the previously recited prior art patent, to position bladder 102 against skin 105 adjacent supraorbital artery 114. In FIG. 10, pad assembly 100 is shown properly positioned on forehead 154 of a person 160 to illustrate the proper orientation of pad assembly 100 on the forehead with regard to its biflex characteristics.

Still referring to FIG. 10 in conjunction with FIG. 7, pad assembly 100 must be adhered to the forehead at the location of the supraorbital artery such that flexible axis 130 is oriented in a substantially vertical direction centered above the artery and rigid axis 132 is horizontally positioned. This orientation allows pad assembly 100 to conform to the contour of the forehead per its design features. Flexibility about flexible axis 130, which is provided by intermediate web portion 128 and outer web portions 136a and 136b, allows the pad assembly to contour to the side to side curvature of the forehead, while properly supporting the bladder against the skin. The pad assembly is sufficiently flexible to contour to the near planar top to bottom features of the forehead while providing a relatively rigid structure for properly retaining the bladder in position to access the supraorbital artery.

In use, pad assembly 100 is first adhered to skin 156 on forehead 154 by adhesive tape 120 in the proper position and orientation to access the supraorbital artery. Next the overall layer of elastic tape 150 is adhered to the exposed portions of the biflex member, the foam frame and portion of skin surrounding the adhesive tape, as shown in FIG. 9. Care should be taken when applying the assembly to the skin to insure that the bonds made by the elastic tape and particularly the adhesive tape are as strong as possible.

Figure 11:
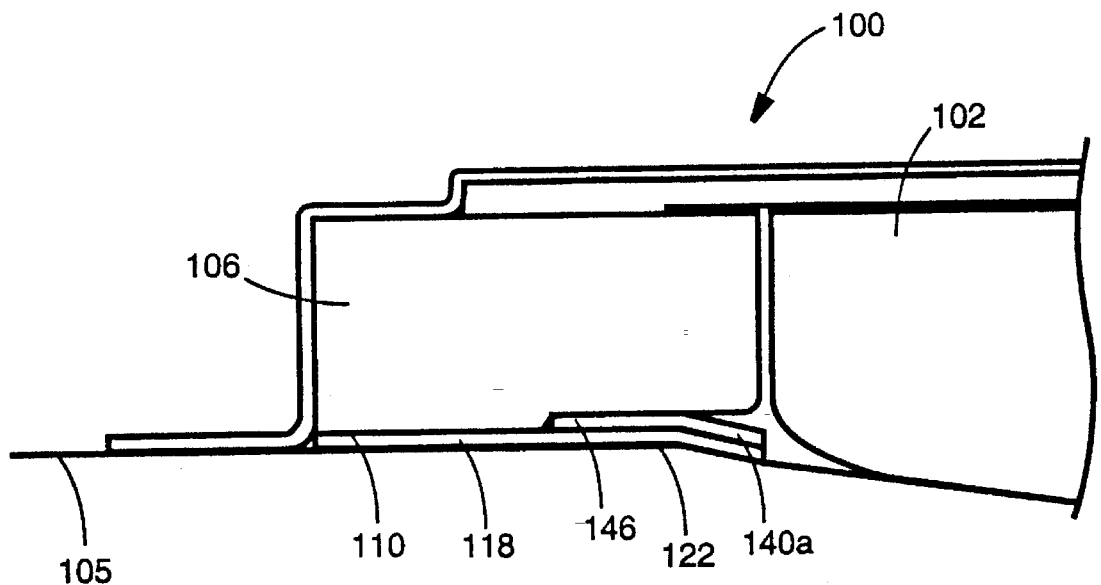
FIG. 11 is a cross-sectional view, in elevation along line 9—9, of a section of the pad assembly of FIG. 8 which is similar to FIG. 9, but with the bladder partially pressurized.

Referring to FIG. 11, as bladder 106 is pressurized during operational use of pad assembly 100, the assembly is designed to respond internally to the forces created by the pressurization in a way which is calculated to maintain adhesive bond 122 between adhesive tape 118 and skin 105 in order to maintain attachment of the pad assembly to the skin. In particular, release bond 146 between release tape segment 140a, which is representative of any number of release tape segments which may be disposed around the bladder, and the portion of lower surface 110 of frame 106 is a weaker adhesive bond, as discussed above, than the bond 122 of adhesive tape 118 to the skin. At a predetermined point during the pressurization of bladder 102, release bond 146 will begin to incrementally separate, as illustrated. As this separation occurs, bond 122 between skin 105 and adhesive tape 110 is maintained, in accordance with the present invention. Continued pressurization of the bladder will cause still further separation of the release bond.

Figure 12:
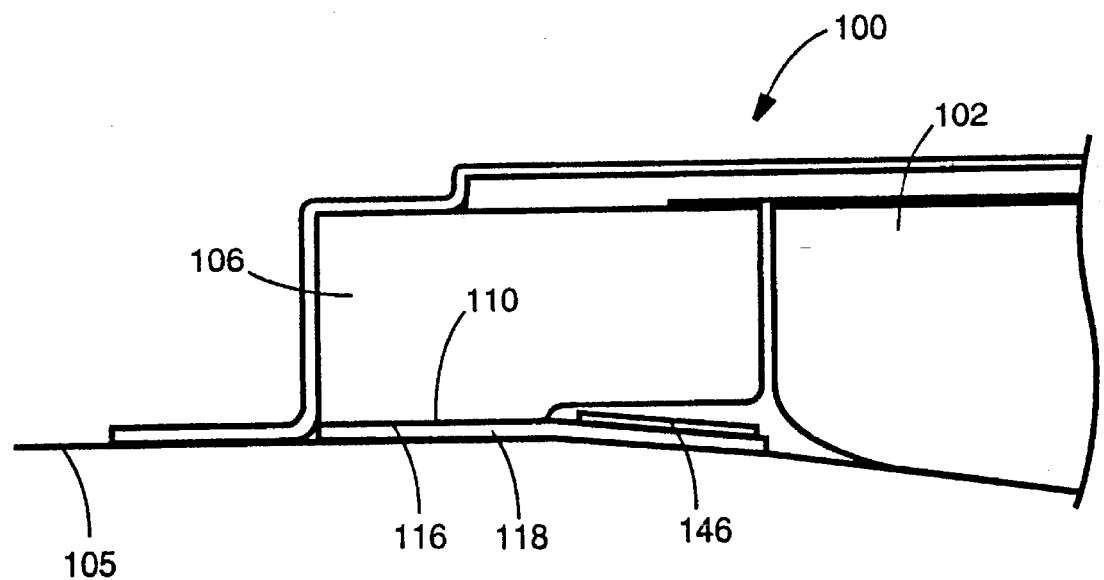
FIG. 12 is a cross-sectional view, in elevation along line 9—9 of a section of the pad assembly of FIG. 8 which also is similar to FIG. 9, but with the bladder fully pressurized.

Referring now to FIG. 12, if pressurization of the bladder does continue, release bond 146 will eventually separate completely, as illustrated. With the complete separation of the release bond the remaining bond directly between lower surface 110 of frame 106 and upper surface 116 of adhesive tape 118 comprises a strong bond capable of supporting the bladder to maintain its communication with the supraorbital artery following complete separation of the release tape segment release bonds.

It should be understood that the present invention may be embodied in many other specific forms without departing from the spirit or scope of the invention. The invention, as disclosed herein, is easily adaptable for use with target arteries other than the supraorbital artery and for use with other blood pressure monitoring techniques. Therefore, the present examples are to be considered as illustrative and not restrictive, and the invention is not to be limited to the details given herein, but may be modified within the scope of the appended claims.

What is claimed is:

1. A pad assembly for use in a system for obtaining certain information about the blood pressure of a given person by a particular blood pressure technique in which a pressurizable pressure transducing bladder is supported on the skin of the person adjacent to and in cooperation with a particular target artery in combination with means for pressurizing the bladder in a controlled way, said pad assembly comprising:

a) said pressure transducing bladder; and
   b) support means including adhesive tape for fixably supporting said bladder in place against the skin adjacent the target artery so that the bladder is in direct contact with the skin and said adhesive tape is directly attached to a portion of the skin adjacent the bladder, said support means further including movement means configured to move at least to a limited extent within a release zone in response to the pressurization of said bladder in a way which prevents said adhesive tape from detaching from the skin as the bladder is pressurized.

2. A pad assembly in accordance with claim 1 wherein said target artery is a supraorbital artery of said person and wherein said pad assembly is specifically configured for attachment adjacent said supraorbital artery.

3. A pad assembly in accordance with claim 1 wherein said support means includes a particular release surface within said release zone and said movement means includes separation means adhesively bonded to said release surface with a bonding strength which is weaker than the bond between the adhesive tape and the skin in order to cause said separation means to incrementally separate from the release surface at least to a limited extent sufficient to keep the adhesive tape attached to the skin in response to pressurization of the bladder.

4. A pad assembly in accordance with claim 1 wherein said movement means is designed so that as the bladder is pressurized to couple with the target artery it incrementally internally separates to at least a limited extent from the rest of the support means sufficient to prevent said adhesive tape from detaching from the skin.

5. A pad assembly in accordance with claim 4 wherein said movement means is further designed so as to reach a point of complete separation from the rest of the support means prior to any detachment of said adhesive tape from the skin without interfering with the proper communication of the bladder with the target artery after said point of separation is attained.

6. A pad assembly in accordance with claim 4 wherein said support means includes a particular release surface within said release zone and wherein said movement means includes means adhesively bonded to said release surface to a predetermined extent which is weaker than the bond of said adhesive tape to the person's skin.

7. A pad assembly in accordance with claim 1 further including a base assembly which, itself, includes said support means, a cover assembly and means connecting said cover assembly to said base assembly for movement of said cover assembly between an opened position separated from said base assembly and a closed position in which the cover assembly is placed directly against the base assembly and serves as a backing for said bladder.

8. A pad assembly in accordance with claim 7 wherein said base assembly further includes an inner frame which is part of said support means and serves as said movement means which is disposed adjacent said bladder and which is adhesively bonded to the cover assembly when the cover assembly is placed in its closed position, said pad assembly further including a particular release surface within said release zone and forming part of said support means and means also forming part of said support means for adhesively bonding said inner frame to said release surface with a bonding strength which is weaker than the bond between the adhesive tape and the skin in order to cause said inner frame to incrementally separate from the release surface at least to a limited extent sufficient to keep the adhesive tape attached to the skin in response to pressurization of the bladder.

9. A pad assembly in accordance with claim 8 wherein said inner frame is designed so as to eventually attain a point of complete separation from said release surface in response to continuing pressurization of the bladder and wherein said cover assembly includes an outer frame adhesively bonded to said base assembly and surrounding the inner frame when the cover assembly is placed in the closed position, said outer frame being capable of supporting said bladder in its operating position coupled to the target artery in the event of complete separation of said inner frame.

10. A pad assembly according to claim 9 wherein said cover assembly includes an outermost cover fixedly supporting said outer frame throughout movement of the cover assembly and bonded to said inner frame at a predetermined lateral distance from the outer frame when the cover assembly is in its closed position such that the outer frame surrounds the inner frame at said predetermined lateral distance to define a stop gap therebetween whereby upon complete separation of the inner frame from said release surface, said outer frame and outermost cover hold the inner frame in place.

11. A pad assembly in accordance with claim 10 further including a plastic sheet member, said member including a cover portion serving as said outermost cover forming said backing in the cover assembly and a base portion interposed between and respectively bonded to at least a portion of the inner frame and at least a portion of the adhesive tape which is bonded to the skin in the base assembly, said sheet member including between the cover and base portions a narrow portion forming said connection means whereby to flexibly connect the cover assembly to the base assembly.

12. A pad assembly in accordance with claim 11 wherein said base portion of the plastic sheet member includes as one surface said release surface adhesively bonded to the inner frame and another surface adhesively bonded to the adhesive tape, the base portion defining an opening therethrough for accommodating the bladder.

13. A pad assembly in accordance with claim 12 wherein said plastic sheet member is rigid PVC.

14. A pad assembly for use in a system for obtaining certain information about the blood pressure of a given person by a particular blood pressure technique in which a pressurizable pressure transducing bladder is supported on the skin of the person adjacent to and in cooperation with a particular target artery in combination with means for pressurizing the bladder in a controlled way, said pad assembly comprising:
  a) a base assembly including:
    i) a plastic base defining an opening for receiving said bladder;
    ii) said bladder positioned over said base and across the opening in the base;
    iii) adhesive skin tape for adhesively attaching the base to said person's skin in conformance to the shape of the skin at the target artery such that the bladder is in direct contact with the skin adjacent the target artery and the adhesive skin tape is attached to a portion of skin adjacent the bladder;
    iv) an inner frame including a top surface and a bottom surface, the bottom surface of which is adhesively bonded to the base by means of an adhesive bond which is not as strong as the bond between the adhesive skin tape and the skin, whereby to establish a release zone between the inner frame and the base causing the inner frame and base to incrementally separate as the bladder is pressurized up to a point of complete separation prior to any separation of the adhesive skin tape from the skin; and
  b) a cover assembly including:
    i) a plastic backing flexibly attached to said plastic base such that said cover assembly is movable between an open position separated from the base assembly prior to attachment to the skin and a closed position directly against the base assembly following attachment of the base assembly to the skin so that said top surface of the inner frame adhesively bonds to the backing; and
    ii) an outer frame affixedly attached to said plastic backing and adhesively bonded to a portion of said adhesive skin tape in the base assembly when the cover assembly is in its closed position so as to conform the cover assembly to the base assembly, said outer frame surrounding the inner frame at a predetermined lateral distance therefrom when said cover assembly is in its closed position and being capable of supporting said bladder in position against the target artery in the event of complete separation of the release zone, and further, said predetermined lateral distance serving as a stop gap whereby to provide an additional expanse of skin stretchable by the bladder in the event of complete separation of the release zone.

15. A pad assembly for use in a system for obtaining certain information about the blood pressure of a given person by a particular blood pressure technique in which a pressurizable pressure transducing bladder is supported on the skin of the person adjacent to and in cooperation with a particular target artery in combination with means for pressurizing the bladder in a controlled way, said pad assembly comprising:

a) said pressure transducing bladder;

b) a base assembly including adhesive tape for supporting said bladder in place against the skin adjacent the target artery;

c) a cover assembly;

d) means connecting said cover assembly to said base assembly for movement of the cover assembly between an open position separated from the base assembly and a closed position in which the cover assembly is placed directly against the base assembly and fixedly attachable thereto to provide a backing for the bladder; and (e) means for adhesively attaching the cover assembly to the base assembly when the cover assembly is in its closed position.

16. A pad assembly in accordance with claim 15 wherein said base assembly, apart from said cover assembly, is sufficiently flexible so as to conform to the contour of the skin adjacent the target artery.

17. A pad assembly in accordance with claim 16 wherein said cover assembly is sufficiently flexible so as to conform to the contoured shape of the base assembly after the base assembly is attached to the person's skin.

18. A pad assembly in accordance with claim 17 wherein said particular artery is a supraorbital artery of said person and wherein said pad assembly is specifically configured for attachment adjacent said supraorbital artery.

19. A pad assembly in accordance with claim 15 wherein said connecting means is integrally formed as part of particular components of said base and cover assemblies and flexibly connects the cover assembly to the base assembly.

20. A pad assembly in accordance with claim 15 wherein said base assembly further includes an inner frame disposed adjacent said bladder and surrounding at least a portion of said bladder and wherein said frame is adhesively bonded to the cover assembly when the cover assembly is in its closed position.

21. A pad assembly in accordance with claim 20 wherein said cover assembly includes an outer frame, said outer frame being adhesively bonded to said base assembly when the cover assembly is placed in the closed position whereby to surround at least a portion of the inner frame.

22. A pad assembly for use in a system for obtaining certain information about the blood pressure of a given person by oscillometry in which a pressurizable pressure transducing bladder is supported on the skin of the person adjacent to and in cooperation with the supraorbital target artery in combination with means for pressurizing the bladder in a controlled way for producing a series of pressure pulses that are responsive to the actual blood pressure within the cooperating target artery and that, upon analysis thereof, provide said information, said pad assembly comprising:

a) said pressure transducing bladder;

b) a base assembly fixedly connected with said bladder and including a base having top and bottom opposing surfaces, said base defining an opening for accommodating the bladder, said base assembly further including adhesive tape bonded directly to the bottom surface of the base for adhesively attaching the base assembly to the skin on said person's forehead with the bladder in position through said opening in direct contact with the skin adjacent the target artery, said base assembly being sufficiently flexible so as to conform to the contour of the person's skin adjacent said target artery;

c) a cover assembly and means for flexibly connecting the cover assembly to the base assembly for movement between a separated open position away from the base assembly and a closed position in which the cover is placed directly against the base assembly, said cover assembly apart from said base assembly being sufficiently flexible so as to conform to the contoured shape of the base assembly after the base assembly is attached to the person's forehead and the cover assembly is moved to its closed position, whereby the cover assembly in its closed position provides a backing for the overall bladder assembly; and d) means for adhesively bonding the cover assembly to the base assembly when the cover assembly is in its closed position.

23. A pad assembly for use in a system for obtaining certain information about the blood pressure of a given person by oscillometry in which a pressurizable pressure transducing bladder is supported on the forehead of the person adjacent to and in cooperation with a supraorbital target artery in combination with means for pressurizing the bladder in a controlled way for producing a series of pressure pulses that are responsive to the actual blood pressure within the cooperating target artery and that, upon analysis thereof, provide said information, said pad assembly including:

a) said pressure transducing bladder;

b) a biflex member including a sheet of plastic material having spaced apart end sections joined by an intermediate narrower section such that the sheet is more flexible in one direction than in a transverse direction, said biflex member also including two stiffening strips respectively attached to the end sections of said sheet member so as to provide further rigidity in said transverse direction;

c) means fixedly attaching said bladder to said biflex member;

d) a frame including top and bottom surfaces, the top surface being bonded to a portion of the biflex member adjacent and surrounding the bladder so as to define an opening therein for the bladder to contact the skin;

e) an adhesive skin tape including top and bottom surfaces wherein the top surface is bonded to portions of the bottom surface of the frame and the bottom surface is bondable to a portion of skin adjacent the bladder such that the bladder is in direct contact with the skin adjacent the target artery and the overall pad assembly is oriented so as to flexibly conform to the contour of the skin at the location of the target artery while providing a sufficiently rigid support for the bladder to keep the bladder in communication with the target artery;

f) release zone tape adhesively bonded between the bottom surface of the frame and the adhesive skin tape in certain predetermined areas such that the bond between the frame and the release zone tape comprises an adhesive bond which will incrementally separate as the bladder is pressurized to maintain the bond between the adhesive tape and the skin; and g) an overall layer of adhesive tape attached to portions of the biflex member, portions of the frame and a portion of skin adjacent the adhesive skin tape, said overall layer of tape having an elastic characteristic whereby to elastically support the pad assembly and thereby the bladder against the target artery during subsequent pressurization of the bladder.

24. In a method of obtaining certain information about the blood pressure of a given person by a particular blood pressure technique in which a pressurizable pressure transducing bladder located adjacent and cooperating with a particular target artery of the person is used in combination with means for pressurizing the bladder in a controlled way, the improvement comprising the steps of:
   a) providing a flexible base assembly including said bladder attached thereto and a cover assembly connected to the base assembly for movement between positions spaced from and directly adjacent said base assembly;
   b) with the cover assembly in its spaced position, adhering said base assembly to said person's skin so that it conforms to the contour thereof and so that the bladder directly contacts the skin adjacent to the target artery; and
   c) thereafter moving said cover assembly to its adjacent position against said base assembly so as to conform with the contour of said base assembly and bond the two together.

25. A method according to the method of claim 23 wherein the target artery is a supraorbital artery and wherein said base assembly is specifically configured for attachment adjacent said supraorbital artery.

26. In a method of obtaining certain information about the blood pressure of a given person by a particular blood pressure technique in which a pressurizable pressure transducing bladder located adjacent and cooperating with a particular target artery of the person is used in combination with means for pressurizing the bladder in a controlled way, the improvement comprising the steps of:
   a) adhesively placing a blood pressure monitoring assembly including said bladder and support means for supporting the bladder on the skin of said person to form an adhesive bond between the skin and the monitoring assembly such that said bladder is brought into direct contact with the skin adjacent said target artery;
   b) pressurizing the bladder to bring the bladder into communication with the target artery; and
   c) providing movement means within said support means configured to move within a release zone in a way which prevents said adhesive tape from detaching from the skin.

27. A method according to the method of claim 26 wherein the target artery is a supraorbital artery and wherein said pad assembly is specifically configured for attachment adjacent said supraorbital artery.

28. A pad assembly for use in a system for obtaining certain information about the blood pressure of a given person by a particular blood pressure technique in which a pressurizable pressure transducing bladder is supported on the skin of the person adjacent to and in cooperation with a particular target artery in combination with means for pressurizing the bladder in a controlled way, said pad assembly comprising:
   a) said pressure transducing bladder;
   b) a base assembly including adhesive tape for supporting said bladder in place against the skin adjacent the target artery;
   c) a cover assembly;
   d) means connecting said cover assembly to said base assembly for movement of the cover assembly between an open position separated from the base assembly and a closed position in which the cover assembly is placed directly against the base assembly and fixedly attachable thereto to provide a backing for the bladder; and
   e) a plastic sheet member, said member including a backing portion serving as said backing for the bladder when the cover assembly is in its closed position and a base portion bonded directly to a portion of said adhesive tape in the base assembly, said sheet member including between the cover and base portions a flexible portion serving as said connecting means whereby to flexibly connect the cover assembly to the base assembly.

29. A pad assembly in accordance with claim 28 wherein said base portion of the plastic sheet member further defines an opening therethrough for accommodating the bladder.

30. A pad assembly in accordance with claim 29 wherein said plastic sheet member is comprised of rigid PVC.

31. A pad assembly for use in a system for obtaining certain information about the blood pressure of a given person by a particular blood pressure technique in which a pressurizable pressure transducing bladder is supported on the forehead of the person adjacent to and in cooperation with a particular target artery in combination with means for pressurizing the bladder in a controlled way, said pad assembly including:
   a) said pressure transducing bladder; and
   b) support means including adhesive tape for fixably supporting said bladder in place against the skin adjacent the target artery so that the bladder is in direct contact with the skin and said adhesive tape is directly attached to a portion of the skin adjacent the bladder, said support means including a biflex member which displays greater flexibility in one predetermined direction than in another predetermined transverse direction, said support means further including movement means configured to move at least to a limited extent within a release zone in response to the pressurization of said bladder in a way which prevents said adhesive tape from detaching from the skin as the bladder is pressurized.

32. A pad assembly in accordance with claim 31 wherein said movement means is designed so that as the bladder is pressurized to couple with the target artery it incrementally internally separates to at least a limited extent from the rest of the support means sufficient to prevent said adhesive tape from detaching from the skin.

33. A pad assembly in accordance with claim 32 wherein said movement means is designed so as to reach a point of complete separation from the rest of the support means prior to any detachment of said adhesive tape from the skin without interfering with the proper communication of the bladder with the target artery after said point of separation is attained.

34. A pad assembly in accordance with claim 33 wherein said support means includes a particular release surface within said release zone and wherein said movement means includes means adhesively bonded to said release surface to a predetermined extent which is weaker than the bond of said adhesive tape to the person's skin.

35. A pad assembly for use in a system for obtaining certain information about the blood pressure of a given person by a particular blood pressure technique in which a pressurizable pressure transducing bladder is supported on the forehead of the person adjacent to and in cooperation with a particular target artery in combination with means for pressurizing the bladder in a controlled way, said pad assembly including:

a) said pressure transducing bladder;

b) support means including adhesive tape for fixably supporting said bladder in place against the skin adjacent the target artery so that the bladder is in direct contact with the skin and said adhesive tape is directly attached to a portion of the skin adjacent the bladder, said support means including a biflex member which displays greater flexibility in one predetermined direction than in another predetermined transverse direction;

c) a frame defining an opening therein accommodating said bladder, said frame being adhesively bonded to the biflex member and to a portion of the adhesive tape with the bladder contacting the skin through the opening to dispose the frame between the biflex member and the adhesive tape; and d) release zone tape adhesively bonded to said frame and to the adhesive tape in certain predetermined areas, and the bond between the frame and the release zone tape being weaker than the bond between the adhesive tape and the skin so as to incrementally separate as the bladder is pressurized to maintain the bond between the adhesive tape and the skin.

36. A pad assembly according to claim 35 wherein the target artery is a supraorbital artery and wherein said pad assembly is specifically configured for attachment adjacent said supraorbital artery.

* * * * *